US008518042B2

(12) United States Patent
Winslow et al.

(10) Patent No.: US 8,518,042 B2
(45) Date of Patent: Aug. 27, 2013

(54) ORTHOPEDIC PLATE ASSEMBLY FOR A DISTAL RADIUS HAVING RE-CONTOURING FEATURES AND METHOD FOR USING SAME

(75) Inventors: Nathan A. Winslow, Warsaw, IN (US); Thomas M. Vanasse, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 212 days.

(21) Appl. No.: 12/907,626

(22) Filed: Oct. 19, 2010

(65) Prior Publication Data
US 2012/0095466 A1 Apr. 19, 2012

(51) Int. Cl.
*A61B 17/58* (2006.01)
*A61B 17/80* (2006.01)

(52) U.S. Cl.
USPC ............... 606/71; 606/280; 606/70; 606/286

(58) Field of Classification Search
USPC ...................... 606/70–71, 280–299
See application file for complete search history.

(56) References Cited

U.S. PATENT DOCUMENTS

| 2,580,821 | A | * | 1/1952 | Toufick ........................ 606/282 |
| 3,824,995 | A | * | 7/1974 | Getscher et al. ............. 606/281 |
| 4,506,662 | A | * | 3/1985 | Anapliotis ...................... 606/62 |
| 5,000,166 | A | * | 3/1991 | Karpf ............................ 606/250 |
| 5,318,567 | A | * | 6/1994 | Vichard ........................... 606/65 |
| 5,380,327 | A | * | 1/1995 | Eggers et al. ................. 606/287 |
| 5,470,333 | A | * | 11/1995 | Ray ................................ 606/261 |
| 5,531,745 | A | * | 7/1996 | Ray ................................ 606/261 |
| 5,591,168 | A | * | 1/1997 | Judet et al. ....................... 606/65 |
| 5,672,176 | A | * | 9/1997 | Biedermann et al. .......... 606/271 |
| 5,681,313 | A | * | 10/1997 | Diez ................................ 606/70 |
| 5,690,631 | A | * | 11/1997 | Duncan et al. ................. 606/281 |
| 5,718,705 | A | | 2/1998 | Sammarco |
| 5,941,878 | A | * | 8/1999 | Medoff ............................ 606/60 |
| 5,964,763 | A | * | 10/1999 | Incavo et al. ..................... 606/71 |
| 6,066,141 | A | * | 5/2000 | Dall et al. ......................... 606/74 |
| 6,123,709 | A | * | 9/2000 | Jones ............................. 606/281 |

(Continued)

FOREIGN PATENT DOCUMENTS
JP 2007190209 A 8/2007

OTHER PUBLICATIONS
DePuy, DVR Anatomic Volar Plating System, Surgical Technique, 2008, pp. 1-17.

(Continued)

*Primary Examiner* — Kevin T Truong
*Assistant Examiner* — Tracy Kamikawa
(74) *Attorney, Agent, or Firm* — Harness, Dickey

(57) ABSTRACT

An orthopedic plate assembly for supporting a bone can include a y-shaped first plate and a second plate separate from the first plate. The first plate can be attached to the bone and have a center line. The first plate can include an elongate body attachable to a first portion of the bone and extending along the center line and first and second arms transversely extending from an end of the body. The first and second arms can define an aperture in the first plate. The second plate can be attached to the bone. The second plate can have a first end and a second end opposite the first end configured to be disposed on and engaged with the first arm and the second arm, respectively. The second plate can be configured to span the aperture transverse to the center line when engaged with the first and second arms.

20 Claims, 8 Drawing Sheets

(56) References Cited

U.S. PATENT DOCUMENTS

| | | | |
|---|---|---|---|
| 6,129,728 A * | 10/2000 | Schumacher et al. | 606/71 |
| 6,224,602 B1 * | 5/2001 | Hayes | 606/296 |
| 6,283,969 B1 * | 9/2001 | Grusin et al. | 606/280 |
| 6,348,052 B1 | 2/2002 | Sammarco | |
| D469,533 S * | 1/2003 | Bryant et al. | D24/155 |
| 6,503,281 B1 * | 1/2003 | Mallory | 623/22.15 |
| 6,506,191 B1 * | 1/2003 | Joos | 606/86 B |
| D469,874 S * | 2/2003 | Bryant et al. | D24/155 |
| 6,652,530 B2 | 11/2003 | Ip et al. | |
| 6,666,867 B2 * | 12/2003 | Ralph et al. | 606/71 |
| 6,712,820 B2 * | 3/2004 | Orbay | 606/286 |
| 6,755,831 B2 * | 6/2004 | Putnam et al. | 606/311 |
| 6,793,658 B2 * | 9/2004 | LeHuec et al. | 606/86 B |
| 6,902,565 B2 * | 6/2005 | Berger et al. | 606/300 |
| 7,033,377 B2 * | 4/2006 | Miller, III | 606/213 |
| 7,090,676 B2 * | 8/2006 | Huebner et al. | 606/71 |
| 7,156,847 B2 * | 1/2007 | Abramson | 606/60 |
| 7,335,204 B2 * | 2/2008 | Tornier | 606/284 |
| 7,537,604 B2 * | 5/2009 | Huebner | 606/281 |
| 7,588,589 B2 * | 9/2009 | Falahee | 606/247 |
| 7,611,513 B2 * | 11/2009 | Deloge et al. | 606/74 |
| 7,635,364 B2 * | 12/2009 | Barrall et al. | 606/70 |
| 7,648,508 B2 * | 1/2010 | Lutz et al. | 606/86 R |
| 7,727,266 B2 * | 6/2010 | Lindemann et al. | 606/289 |
| 7,731,718 B2 * | 6/2010 | Schwammberger et al. | 606/71 |
| 7,758,616 B2 * | 7/2010 | LeHuec et al. | 606/246 |
| 7,857,837 B2 * | 12/2010 | Lieponis | 606/280 |
| 7,867,260 B2 * | 1/2011 | Meyer et al. | 606/280 |
| 7,988,691 B2 * | 8/2011 | Schulze et al. | 606/71 |
| 8,048,076 B2 * | 11/2011 | Michelson | 606/71 |
| 8,070,749 B2 * | 12/2011 | Stern | 606/71 |
| 8,147,493 B2 * | 4/2012 | Dutoit et al. | 606/65 |
| 8,177,819 B2 * | 5/2012 | Huebner et al. | 606/281 |
| 8,226,688 B2 * | 7/2012 | Alain | 606/248 |
| 8,231,625 B2 * | 7/2012 | Graham et al. | 606/71 |
| 8,257,355 B2 * | 9/2012 | Chin et al. | 606/70 |
| 2002/0062127 A1 * | 5/2002 | Schumacher et al. | 606/70 |
| 2002/0143338 A1 * | 10/2002 | Orbay et al. | 606/69 |
| 2002/0183754 A1 * | 12/2002 | Michelson | 606/70 |
| 2003/0036759 A1 * | 2/2003 | Musso | 606/69 |
| 2003/0149434 A1 * | 8/2003 | Paul | 606/71 |
| 2003/0163132 A1 * | 8/2003 | Chin | 606/61 |
| 2004/0102778 A1 * | 5/2004 | Huebner et al. | 606/71 |
| 2004/0116931 A1 * | 6/2004 | Carlson | 606/70 |
| 2004/0167521 A1 * | 8/2004 | De Windt | 606/69 |
| 2004/0181226 A1 * | 9/2004 | Michelson | 606/61 |
| 2004/0220571 A1 * | 11/2004 | Assaker et al. | 606/69 |
| 2004/0225291 A1 * | 11/2004 | Schwammberger et al. | 606/71 |
| 2005/0027293 A1 * | 2/2005 | LeHuec et al. | 606/61 |
| 2005/0234458 A1 * | 10/2005 | Huebner | 606/69 |
| 2005/0240187 A1 * | 10/2005 | Huebner et al. | 606/69 |
| 2005/0245931 A1 * | 11/2005 | Orbay | 606/69 |
| 2005/0283152 A1 * | 12/2005 | Lindemann et al. | 606/61 |
| 2006/0089648 A1 * | 4/2006 | Masini | 606/69 |
| 2006/0116681 A1 * | 6/2006 | Bert | 606/69 |
| 2006/0173458 A1 * | 8/2006 | Forstein et al. | 606/69 |
| 2006/0200151 A1 * | 9/2006 | Ducharme et al. | 606/73 |
| 2006/0217722 A1 * | 9/2006 | Dutoit et al. | 606/69 |
| 2006/0264949 A1 * | 11/2006 | Kohut et al. | 606/69 |
| 2007/0043366 A1 * | 2/2007 | Pfefferle et al. | 606/69 |
| 2007/0123886 A1 * | 5/2007 | Meyer et al. | 606/70 |
| 2007/0299448 A1 * | 12/2007 | Chin et al. | 606/69 |
| 2008/0009872 A1 * | 1/2008 | Vaughen et al. | 606/71 |
| 2008/0140127 A1 * | 6/2008 | Vasta et al. | 606/280 |
| 2008/0161861 A1 * | 7/2008 | Huebner | 606/286 |
| 2009/0036931 A1 * | 2/2009 | Pech et al. | 606/280 |
| 2009/0043341 A1 * | 2/2009 | Tyber et al. | 606/283 |
| 2009/0069851 A1 * | 3/2009 | Gillard et al. | 606/280 |
| 2009/0270861 A1 * | 10/2009 | Flandry, Jr. | 606/71 |
| 2009/0275987 A1 * | 11/2009 | Graham et al. | 606/280 |
| 2009/0281577 A1 * | 11/2009 | Graham et al. | 606/280 |
| 2009/0287258 A1 * | 11/2009 | Vannemreddy | 606/298 |
| 2009/0306724 A1 * | 12/2009 | Leither et al. | 606/289 |
| 2009/0318920 A1 * | 12/2009 | Jacobs | 606/70 |
| 2010/0057132 A1 * | 3/2010 | Graham et al. | 606/280 |
| 2010/0057133 A1 * | 3/2010 | Simon | 606/280 |
| 2010/0137868 A1 * | 6/2010 | Orbay et al. | 606/71 |
| 2010/0152783 A1 * | 6/2010 | Borostyankoi et al. | 606/281 |
| 2010/0179599 A1 * | 7/2010 | Derouet et al. | 606/280 |
| 2010/0262194 A1 * | 10/2010 | Wagner et al. | 606/286 |
| 2010/0268283 A1 * | 10/2010 | Orbay | 606/281 |
| 2010/0292696 A1 * | 11/2010 | Chantelot et al. | 606/70 |
| 2010/0324602 A1 * | 12/2010 | Huebner et al. | 606/280 |
| 2011/0022049 A1 * | 1/2011 | Huebner et al. | 606/71 |
| 2011/0137314 A1 * | 6/2011 | Kuster et al. | 606/70 |
| 2011/0218533 A1 * | 9/2011 | Prandi et al. | 606/71 |
| 2011/0218535 A1 * | 9/2011 | Wang et al. | 606/71 |
| 2011/0276097 A1 * | 11/2011 | Raven et al. | 606/284 |
| 2011/0319894 A1 * | 12/2011 | Gupta | 606/70 |
| 2012/0226279 A1 * | 9/2012 | Lutz et al. | 606/70 |

OTHER PUBLICATIONS

Medartis, Distal Radius System 2.5, Surgical Technique, APTUS Wrist, Feb. 2011, pp. 1-19.

Stryker, The New Comprehensive Stryker Variax Distal Radius Locking Plate System, Operative Technique, 2009, pp. 1-19.

Synthes, 2.4 mm Variable Angle LP Distal Radius System for Fragment-Specific Fracture Fixation With Variable Angle Locking Technology, Technique Guide, 2008, pp. 1-41.

Zimmer, Periarticular Distal Radial Locking Plates, Surgical Technique, 2009, pp. 1-25.

* cited by examiner

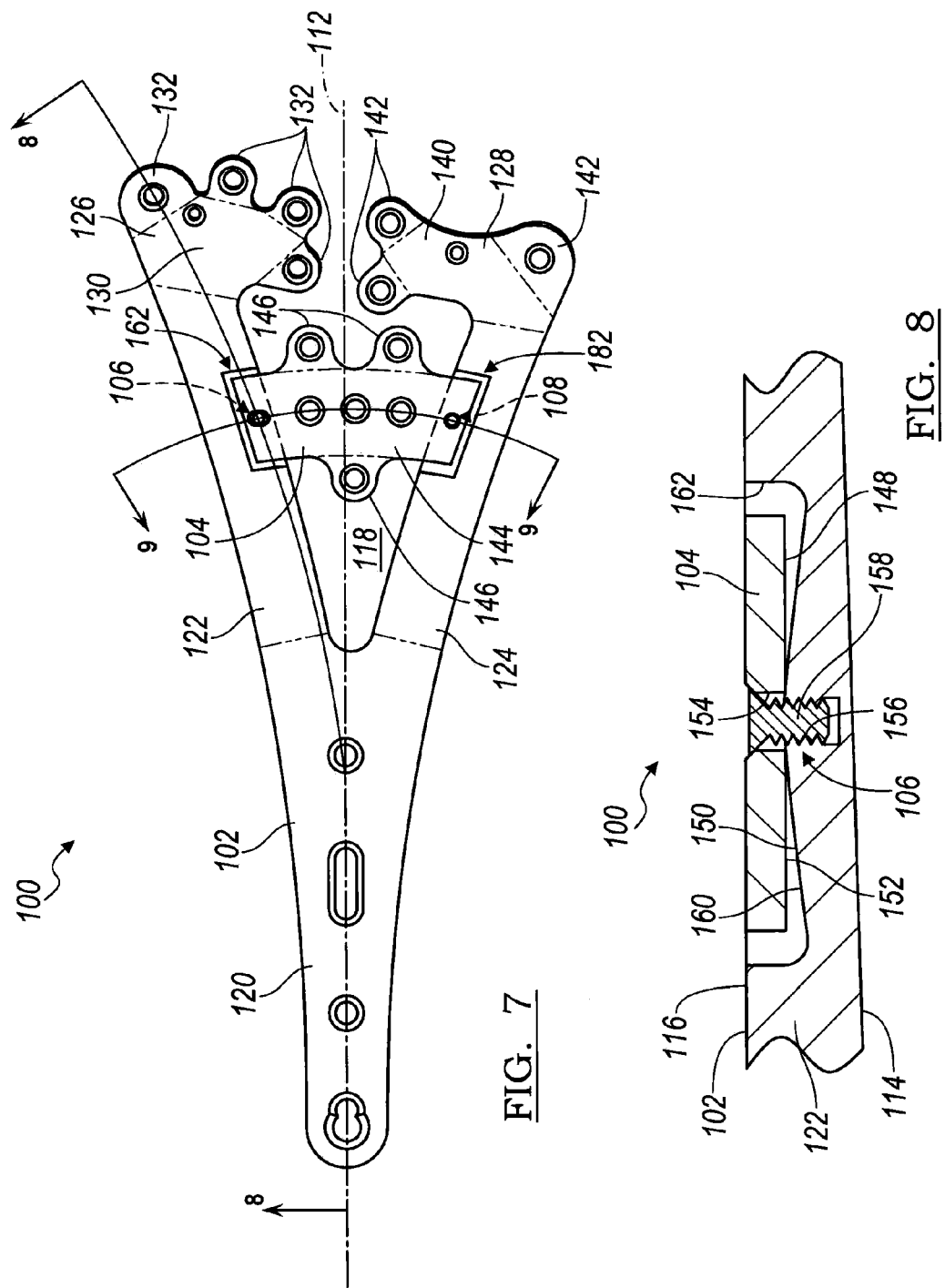

ORTHOPEDIC PLATE ASSEMBLY FOR A DISTAL RADIUS HAVING RE-CONTOURING FEATURES AND METHOD FOR USING SAME

FIELD

The present disclosure relates to orthopedic plates used to treat a fractured radius, and more particularly, to orthopedic plates that can be contoured to match the external surface of the radius.

BACKGROUND

This section provides background information related to the present disclosure which is not necessarily prior art.

Bones can become fractured due to high impact or stress, or as a result of a medical condition that weakens the bones, such as osteoporosis. For example, the force of a fall on an outstretched hand can result in a distal radius fracture. Incomplete fractures are fractures in which bone fragments are still partially joined, while complete fractures are fractures in which the bone fragments are completely separated. Depending on the severity, treatment of fractured bones can include aligning the bone fragments to their natural positions, called reduction, and maintaining the natural positions while the bones heal, called immobilization.

Immobilization can be achieved using non-operative procedures and/or surgical procedures. In non-operative procedures, casts, splints, or other external fixation devices can maintain the natural positions by immobilizing joints above and below the fractured bone. When treated through surgery, orthopedic nails, screws, plates, and wires can hold the bone fragments together more directly. Orthopedic plates approximating the contour of the fractured bone can attach to the bone fragments and fix the bone fragments in their natural positions. However, due to variation in the contour of bones and variation in fracture patterns, orthopedic plates having improved contouring capability are desired. Through improved contouring, the bone fragments can be fixed in positions more closely matching their natural positions.

SUMMARY

This section provides a general summary of the disclosure, and is not a comprehensive disclosure of its full scope or all of its features.

An orthopedic plate assembly for supporting a bone can include a y-shaped first plate and a second plate separate from the first plate. The first plate can be attachable to the bone and have a center line. The first plate can include an elongate body attachable to a first portion of the bone and extending along the center line, a first arm transversely extending from an end of the body, and a second arm transversely extending from the end of the body. The first and second arms can define an aperture in the first plate.

The second plate can be attachable to the bone. The second plate can have a first end configured to be disposed on and engaged with the first arm, and a second end opposite the first end configured to be disposed on and engaged with the second arm. The second plate can be configured to span the aperture transverse to the center line when engaged with the first and second arms.

An orthopedic plate assembly for supporting a fractured radius can include a first plate, a second plate separate from the first plate, and a first engagement member. The first plate can be attachable to a first bone fragment and a second bone fragment of the radius and have a centerline. The first plate can include an elongate body attachable to the first fragment and extending along the center line, a first arm transversely extending from an end of the body, and a second arm transversely extending from the end of the body. The second plate can include a first transverse surface on a first end engageable with a second transverse surface of the first arm, and a third transverse surface on a second end opposite the first end engageable with a fourth transverse surface of the second arm. The second plate can be configured to span the aperture transverse to the center line when engaged with the first and second arms.

The first engagement member can be configured to constrain relative translational movement between the first and second plates in at least two perpendicular directions when engaged. The first engagement member can include a first bearing component coupled to the first transverse surface of the second plate, and a second bearing component coupled to the second transverse surface of the first arm and directly engageable with the first bearing component.

A method for supporting a fractured radius using an orthopedic plate assembly can include exposing the radius, selecting a first plate and selectively re-contouring the first plate, and attaching the first plate to a first portion of the radius using a first attachment device. The first plate can have a center line and include a body extending along the center line, a first arm transversely extending from an end of the body and including a first transverse surface, and a second arm transversely extending from the end of the body and including a second transverse surface. The first and second arms can define an aperture in the first plate.

The method can further include selecting a second plate and selectively re-contouring the second plate. The second plate can have a first end including a third transverse surface engageable with the first transverse surface of the first arm, and a second end opposite the first end including a fourth transverse surface engageable with the second transverse surface of the second arm. The method can further include engaging the second plate with the first plate at a predetermined longitudinal position within the aperture by engaging the third and fourth transverse surfaces of the second plate with the first and second transverse surfaces of the second plate, respectively. The method can further include attaching the second plate to at least one of the first plate and a second portion of the radius.

Further areas of applicability will become apparent from the description provided herein. The description and specific examples in this summary are intended for purposes of illustration only and are not intended to limit the scope of the present teachings.

DRAWINGS

The drawings described herein are for illustrative purposes only of selected examples and not all possible implementations, and are not intended to limit the scope of the present teachings.

FIG. 7 is a top view of the plate assembly of FIG. 6;

FIG. 8 is a cross-sectional side view of a portion of the plate assembly of FIG. 6 taken along line 8-8;

Corresponding reference numerals indicate corresponding parts throughout the several views of the drawings.

DESCRIPTION OF VARIOUS EMBODIMENTS

Examples according to the present teachings will now be described more fully with reference to the accompanying drawings. The examples are provided so that this disclosure will be thorough, and will fully convey the scope to those who are skilled in the art. Numerous specific details are set forth such as examples of specific components, devices, and methods, to provide a thorough understanding of the present teachings. It will be apparent to those skilled in the art that specific details need not be employed, that examples may be embodied in many different forms and that neither should be construed to limit the scope of the disclosure. In some examples, well-known processes, well-known device structures, and well-known technologies are not described in detail.

With reference to FIGS. 1-5, an exemplary orthopedic plate assembly 10 for internal fixation of two or more fragments 12, 14 of a fractured bone 16 is presented. For clarity, various features of the plate assembly 10 will be described with reference to coordinate axes shown in FIG. 2. The plate assembly 10 can be used in a bone plate system used for internal fixation of the fragments 12, 14. In the present example, the plate assembly 10 is configured to attach to the distal, volar aspect of a fractured radius of a right arm. Although not specifically shown, it will be appreciated that the plate assembly 10 can be configured, for example in a mirror image, to attach to a radius of a left arm. It will be further appreciated that the present teachings apply equally to orthopedic plates for attachment with other bones.

Figure 1:
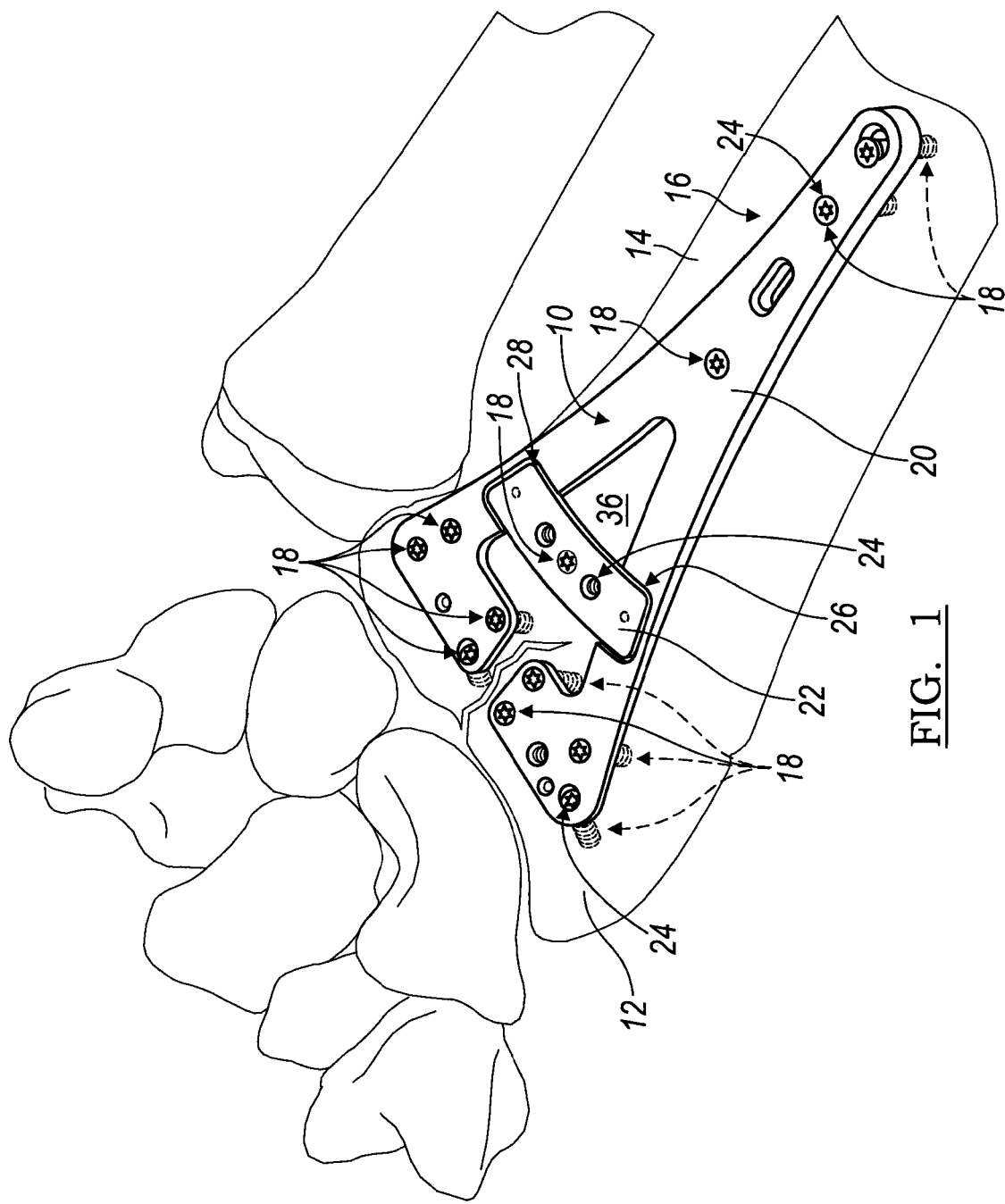
FIG. 1 is an environmental illustration of an orthopedic plate assembly according to the present disclosure coupled to a distal radius.
Figure 2:
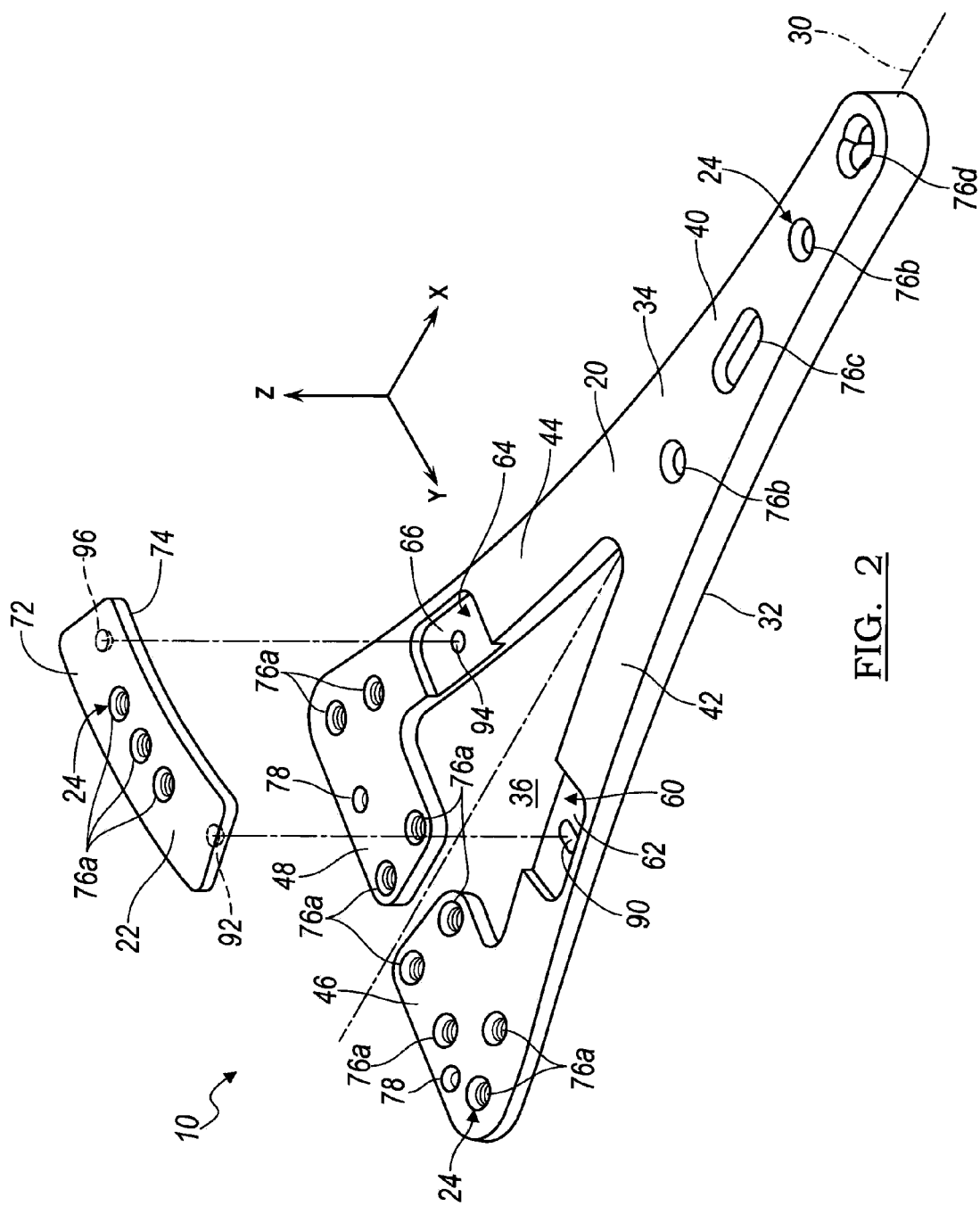
FIG. 2 is an exploded perspective view of the plate assembly of FIG. 1.

The plate assembly 10 can be secured to the bone 16, and more particularly, to each of the fragments 12, 14, using various attachment devices. Suitable attachment devices include, but are not limited to, orthopedic nails, bone screws, and k-wires. For example, the plate assembly 10 can be secured to the bone 16 using a combination of bone screws 18 as shown (FIG. 1).

Generally, the plate assembly 10 can include a Y-shaped, bifurcated plate member 20 and a support member 22, each having a plurality of holes 24 configured to receive various attachment devices, such as the bone screws 18. The plate member 20 and the support member 22 can be independently re-contoured and attached to the bone 16 using the holes 24 and various attachment devices. In an exemplary surgical procedure, the plate member 20 can be attached to one or both the fragments 12, 14. Subsequently, the support member 22 can be attached to the plate member 20 and/or at least one of the fragments 12, 14. When attached, the support member 22 can engage the plate member 20. Through engagement, the support member 22 can assist the plate member 20 in holding the fragments 12, 14 at or near their natural positions by assisting the plate member 20 in retaining a desired shape.

In various implementations, the plate assembly 10 can include a first engagement member 26 and a second engagement member 28 at interfaces between the plate member 20 and the support member 22. The first and second engagement members 26, 28 can cooperate and thereby form joints between the plate member 20 and the support member 22. The joints, discussed in more detail below, can constrain relative translational movement between the plate member 20 and the support member 22 and thereby assist the plate member 20 in retaining the desired shape.

The support member 22 and the plate member 20 can be formed to be malleable or bendable, yet exhibit sufficient stiffness to support the bone 16 in their respective re-contoured shapes. The plate member 20 and the support member 22 can include contouring regions including features that enable the independent re-contouring of the plate member 20 and the support member 22 prior to and/or during the surgical procedure. Through re-contouring, the shapes of the plate member 20 and the support member 22 can be adjusted to more closely match the unique contour of the bone 16 of a particular patient. Re-contouring can also be used to modify the trajectories of one or more of the bone screws 18. Through engagement, the support member 22 and the plate member 20 can cooperate to increase the stiffness of the overall plate assembly 10, and thereby assist in the retention of the re-contoured shapes.

The plate member 20 and the support member 22 can be composed of various biocompatible materials of a suitable modulus of elasticity for providing the plate member 20 and the support member with the re-contouring and shape retention features. Suitable materials include, but are not limited to, biocompatible metals including stainless steel, titanium, and titanium-based alloys. The plate member 20 and the support member 22 can be formed using various manufacturing methods including, but not limited to, casting, machining, and forging.

The plate member 20 can generally be smooth and thin and can have a length along a center line 30. In FIGS. 1-5, the center line 30 is shown to extend along the x-axis. The plate member 20 can be formed to have a pre-contoured shape based on a typical morphology of the bone to which the plate member 20 is to be secured. Generally, the plate member 20 can include a bone engaging surface 32, an outer surface 34, an aperture 36, and a predetermined number and arrangement of the holes 24.

The plate member 20 can have a thickness between the bone engaging surface 32 and the outer surface 34. The thickness can vary along the length to provide the plate member 20 with regions of varying malleability and can depend on the surrounding anatomy. For example, the thickness can taper to provide the plate member 20 with progressively more malleability from one end to an opposite end. The thickness can further vary to provide the plate member 20 with a low profile that enables the plate member 20 to be positioned between various structures of the anatomy such as, for example, between the bone 16 and tendons of the surrounding anatomy. According to the present example, the thickness can taper from a first thickness of around 3.0 millimeters (mm) on one end (e.g., a proximal end) to a second thickness of around 2.0 mm on an opposite (e.g., distal end) as shown.

The plate member 20 can further include an elongated body 40, a first arm 42, a second arm 44, a first tab 46, and a second tab 48 that are formed to provide the plate member 20 with a y-shape. The body 40 can include a first contouring region 50. The first and second arms 42, 44 can include second and third contouring regions 52a, 52b, respectively. The first and second tabs 46, 48 can include fourth and fifth contouring regions 54a, 54b, respectively. The first contouring region 50 can share boundaries 56a, 56b with the second and third contouring regions 52a, 52b, respectively. The second and third contouring regions 52a, 52b can share boundaries 58a, 58b with the fourth and fifth contouring regions 54a, 54b, respectively.

The bone engaging surface 32 can be a first major surface configured to directly engage the bone 16. The outer surface 34 can be a second major surface opposite the bone engaging surface 32 and can be configured to allow the tendons of the surrounding anatomy to glide smoothly over the plate member 20 during implantation and post-surgery. For example, the outer surface 34 can generally be a smooth surface having chamfered edges. In FIGS. 1-5, the bone engaging surface 32 and the outer surface 34 are shown as including substantially planar surfaces for simplicity. It will be appreciated that the bone engaging surface 32 and the outer surface 34 can include other contoured surfaces. The bone engaging surface 32 and the outer surface 34 can be further configured to inhibit tissue adhesion with the plate member 20. In an exemplary implementation, the bone engaging surface 32 and the outer surface 34 can be polished and/or anodized surfaces.

The outer surface 34 can define a rectangular first recess 60 having a first bottom surface 62, and a rectangular second recess 64 having a second bottom surface 66. The bottom surfaces 62, 66 can extend transverse to the center line 30. The first recess 60 can be formed in the first arm 42 and can nestingly receive one end of the support member 22. The second recess 64 can be formed in the second arm 44 and can nestingly receive an opposite end of the support member 22. The first and second recesses 60, 64 can be sized to provide gaps 68, 70 between the support member 22 and the plate member 20, when engaged with one another. The gaps 68, 70 can be sized to accommodate variation in the relative positions of the plate member 20 and the support member 22 due to re-contouring. The first and second recesses 60, 64 can be further sized to allow an outer surface 72 of the support member 22 to lie generally flush or co-planar with an adjoining portion of the outer surface 34 when the support member 22 is engaged with the plate member 20.

The first and second bottom surfaces 62, 66 can be disposed between the bone engaging surface 32 and the outer surface 34. The first and second bottom surfaces 62, 66 can engage an inner surface 74 of the support member 22 that faces the outer surface 34 when the support member 22 is engaged with the plate member 20. The first and second bottom surfaces 62, 66 can directly engage the inner surface 74. Alternatively, or additionally, the first and second bottom surfaces 62, 66 can engage the support member 22 via the first and second engagement members 26, 28, as illustrated by the present example. The first and second bottom surfaces 62, 66 can form a portion of the first and second engagement members 26, 28.

Generally, the aperture 36 can extend between the first and second arms 42, 44 and can be triangularly shaped. The aperture 36 can provide access for viewing the fracture site and/or applying a bone graft or other biologic material during the surgical procedure, when the plate member 20 is secured to the bone 16. The aperture 36 can be sized and disposed at a predetermined location of the plate member 20. The size and location can be predetermined based on the morphology of the bone 16 and the associated fracture patterns.

The holes 24 included with the plate member 20 can be configured to receive the various attachment devices used to secure the plate member 20 to the bone 16. Accordingly, the holes 24 can extend through the outer surface 34 and the bone engaging surface 32, and can be of various sizes and configurations. The holes 24 can have a predetermined number and predetermined arrangement based on typical fracture patterns of the bone 16. The holes 24 can provide predetermined trajectories or trajectory ranges for the attachment devices. Through re-contouring of the plate member 20, the trajectories and the trajectory ranges can be adjusted.

For exemplary purposes, a plurality of bone screw holes 76a, 76b, 76c, 76d and K-wire holes 78 of various configurations are illustrated. The holes 76a can be chamfered, cylindrical holes configured with threads that threadingly engage respective bone screws and provide a predetermined trajectory. The holes 76b can be chamfered, non-threaded cylindrical holes configured to receive respective bone screws and provide predetermined trajectory ranges. The hole 76c can be a chamfered, non-threaded slot configured to receive a respective bone screw at various positions longitudinal along the slot and provide a predetermined trajectory range. The hole 76d can be a chamfered, non-threaded slot having an enlarged circular end. The enlarged circular end can be configured to allow the plate member 20 to be positioned over a respective bone screw previously threaded into the bone 16 and translated to bring the bone screw into engagement with the hole 76d. The K-wire holes 78 can be chamfered, non-threaded cylindrical holes configured to receive respective K-wires.

The body 40 can be attached to a first portion of the bone 16 associated with one of the fragments 12, 14. According to the present example, the body can be attached to the fragment 14. When the bone 16 is a long bone, such as in the present example, the body 40 can attach to a diaphyseal portion of the bone 16. The body 40 can include a portion of the bone engaging surface 32, a portion of the outer surface 34, and a predetermined number of the holes 24.

The body 40 can form the first contouring region 50 and can be sized to provide the plate member 20 with a predetermined first stiffness in the first contouring region 50. For example, a thickness (z-direction) and a width (y-direction) of the body 40 can be selected to provide the first contouring region 50 with the first stiffness. In various implementations, the body 40 can be relatively rigid when compared with the first and second arms 42, 44 and the first and second tabs 46, 48. The thickness, the width, and the first stiffness can vary along the length of the body 40. In the present example, the thickness gradually decreases between a terminal end and an opposite end connected to the first and second arms 42, 44. The width gradually increases between the terminal end and the first and second arms 42, 44. Thus, the first stiffness in the z-direction gradually decreases between the terminal end and the first and second arms 42, 44.

Figure 3:
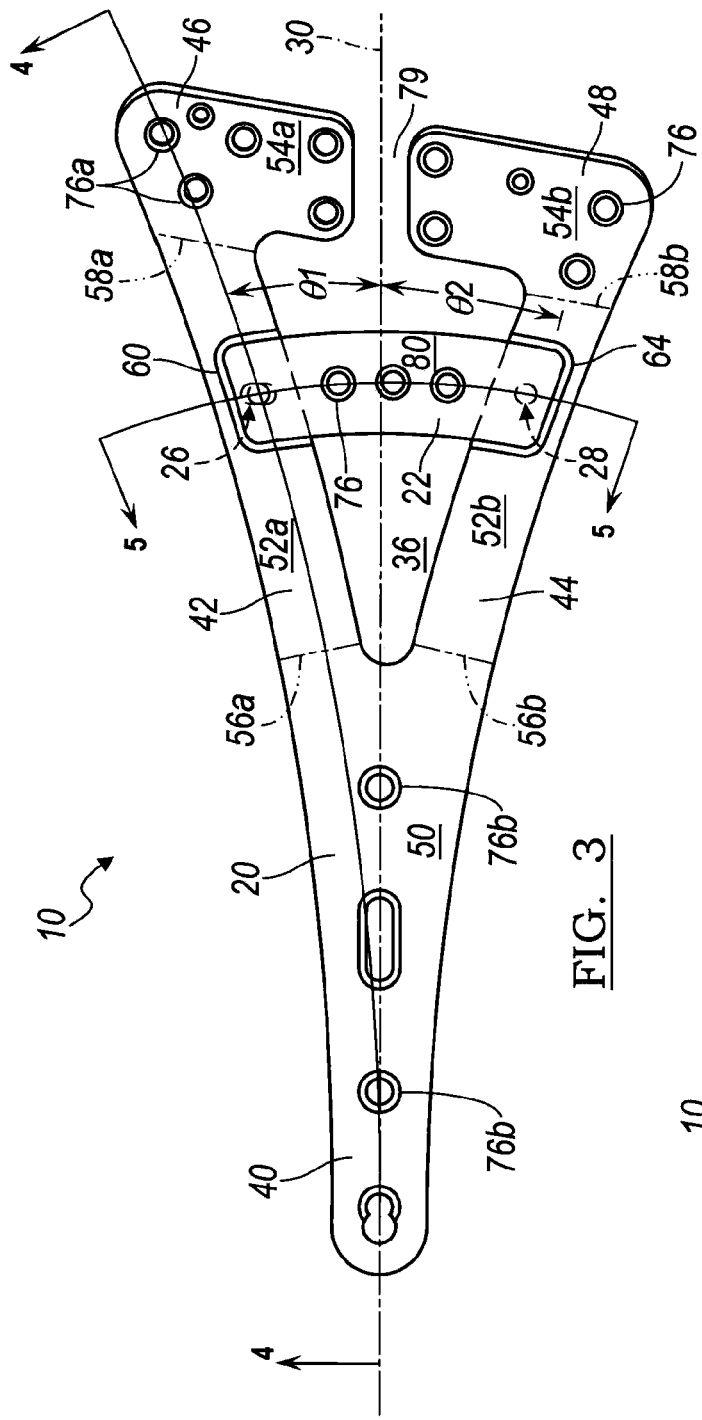
FIG. 3 is a top view of the plate assembly of FIG. 1.

The first arm 42 can extend from an end of the body 40 away from the center line 30 in a first transverse direction (e.g., y-direction and/or z-direction). The first arm 42 can extend at a predetermined angle $\theta 1$ with respect to the center line 30 (FIG. 3). In various implementations, the first arm 42 can be curved and the angle $\theta 1$ can increase between the body 40 and the first tab 46. In various implementations, the angle $\theta 1$ can be between zero degrees and 90 degrees. More specifically, the angle $\theta 1$ can be between zero degrees and 45 degrees, and even more specifically between zero degrees and 25 degrees.

The first arm 42 can extend between and can connect the body 40 and the first tab 46. The first arm 42 can engage a portion of the bone 16. The first arm 42 can engage the support member 22 via the first recess 60 and the first bottom surface 62. The first arm 42 can include a portion of the bone engaging surface 32 and a portion of the outer surface 34. Although not shown, the first arm 42 can include a predetermined number of the holes 24.

The first arm 42 can form the second contouring region 52a and can be sized to provide the plate member 20 with a predetermined second stiffness in the second contouring region 52a. A thickness, a width, and the second stiffness can vary along a length of the first arm 42. In the present example, the thickness, in general, gradually decreases between the body 40 and the first tab 46 and the width is generally constant along the length. Accordingly, the second stiffness gradually decreases between the body 40 and the first tab 46. The first arm 42 can have a predetermined length selected based on the particular bone to which the plate member 20 is to be attached and the associated fracture patterns. The length of the first arm 42 can be the same as or different from the length of the body 40.

The second arm 44 can extend from the end of the body 40 away from the center line 30 in a second transverse direction. The second arm 44 can extend at a predetermined angle θ2 with respect to the center line 30 (FIG. 3). In various implementations, the second arm 44 can be curved and the angle θ2 can increase between the body 40 and the second tab 48. In various implementations, the angle θ2 can be between zero degrees and 90 degrees. More specifically, the angle θ2 can be between zero degrees and 45 degrees, and even more specifically between zero degrees and 25 degrees.

The second arm 44 can extend between and can connect the body 40 and the second tab 48. The second arm 44 can engage a portion of the bone 16. The second arm 44 can engage the support member 22 via the second recess 64 and the second bottom surface 66. The second arm 44 can include a portion of the bone engaging surface 32 and a portion of the outer surface 34. Although not shown, the second arm 44 can include a predetermined number of the holes 24.

The second arm 44 can form the third contouring region 52b and can be sized to provide the plate member 20 with a predetermined third stiffness in the third contouring region 52b. A thickness, a width, and the third stiffness can vary along a length of the second arm 44. In the present example, the thickness, in general, gradually decreases between the body 40 and the second tab 48 and the width is generally constant along the length. Accordingly, the third stiffness in the z-direction gradually decreases between the body 40 and the first tab 46. The second arm 44 can have a predetermined length selected based on the particular bone to which the plate member 20 is to be attached and the associated fracture patterns. The length of the second arm 44 can be the same as or different from the length of the first arm 42 and the length of the body 40.

Figure 4:
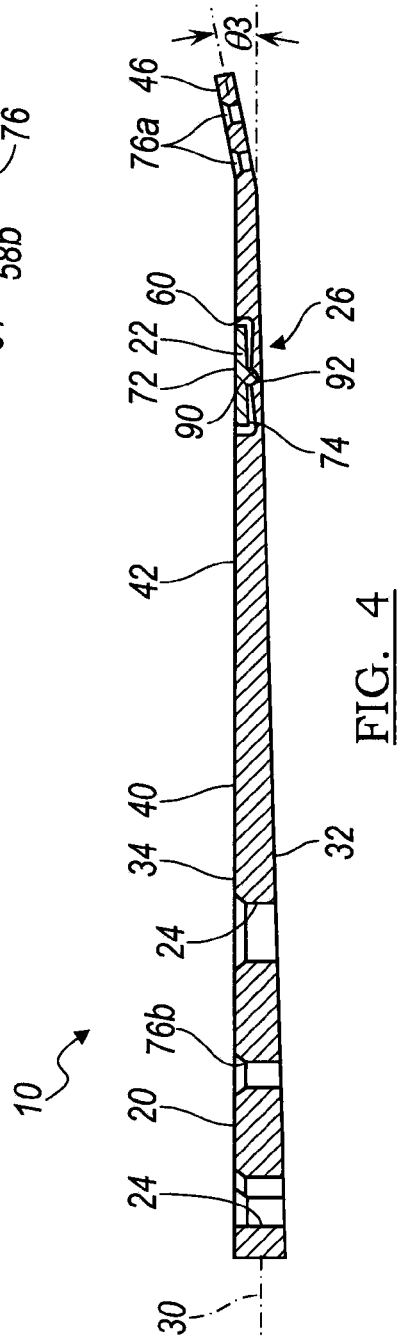
FIG. 4 is a cross-sectional side view of the plate assembly of FIG. 1 taken along line 4-4.

The first tab 46 can extend from an end of the first arm 42 opposite the body 40, and can extend transverse to the first arm 42. The first tab 46 can extend at a predetermined angle θ3 with respect to the center line 30 (FIG. 4). In various implementations, the angle θ3 can be between zero degrees and 90 degrees. More specifically, the angle θ3 can be between zero degrees and 45 degrees, and even more specifically between zero degrees and 25 degrees. The angle θ3 can be varied through re-contouring of the first tab 46.

The first tab 46 can extend towards or away from the center line 30. The first tab 46 can be attached to a second portion of the bone 16 associated with one of the fragments 12, 14. Depending on the fracture pattern, the first tab 46 can be attached to the same or a different fragment than the fragment to which the body 40 is attached. According to the present example, the first tab 46 can be attached to the same fragment 14 as the body 40. When the bone to which the plate member 20 is to be secured is a long bone, the first tab 46 can be attached to an epiphyseal portion of the bone.

The first tab 46 can include a portion of the bone engaging surface 32, a portion of the outer surface 34, and a predetermined number of the holes 24. The number and arrangement of the holes 24 can be based on the typical fracture patterns of the bone 16. The first tab 46 can form the fourth contouring region 54a and can be sized to provide the plate member 20 with a predetermined fourth stiffness in the fourth contouring region 54a. The first tab 46 can have a predetermined width (y-direction) selected based on the particular bone to which the plate member 20 is to be attached and the associated fracture patterns.

The second tab 48 can be separated from the first tab 46 by a gap 79. The second tab 48 can extend from an end of the second arm 44 opposite the body 40, and can extend transverse to the second arm 44. The second tab 48 can extend at a predetermined angle with respect to the center line 30. In the present example, the second tab 48 can extend at the same angle θ3 as the first tab 46. In various implementations, the angle can be between zero degrees and 90 degrees. More specifically, the angle can be between zero degrees and 45 degrees, and even more specifically between zero degrees and 25 degrees. The angle can be varied through re-contouring of the second tab 48.

The second tab 48 can extend towards or away from the center line 30. The second tab 48 can extend substantially parallel to the first tab 46. The second tab 48 can be attached to a third portion of the bone 16 associated with one of the fragments 12, 14. Depending on the fracture pattern, the second tab 48 can be attached to the same or different fragments than the fragment to which the body 40 is attached and the fragment to which the first tab 46 is attached. According to the present example, the second tab 48 can be attached to a different fragment, the fragment 12, than the fragment 14 to which the body 40 and the first tab 46 is attached. When the bone to which the plate member 20 is to be attached is a long bone, the second tab 48 can attach to the epiphyseal portion of the bone.

The second tab 48 can include a portion of the bone engaging surface 32, a portion of the outer surface 34, and a predetermined number of the holes 24. The number and arrangement of the holes 24 can be based on the typical fracture patterns of the bone 16 and, thus, can be different than the number and arrangement of the holes 24 of the first tab 46. The second tab 48 can form the fifth contouring region 54b and can be sized to provide the plate member 20 with a predetermined fifth stiffness in the fifth contouring region. The second tab 48 can have a predetermined width (y-direction) selected based on the particular bone to which the plate member 20 is to be attached and the associated fracture patterns. The width of the second tab 48 can be the same as or different from the width of the first tab 46.

Figure 5:
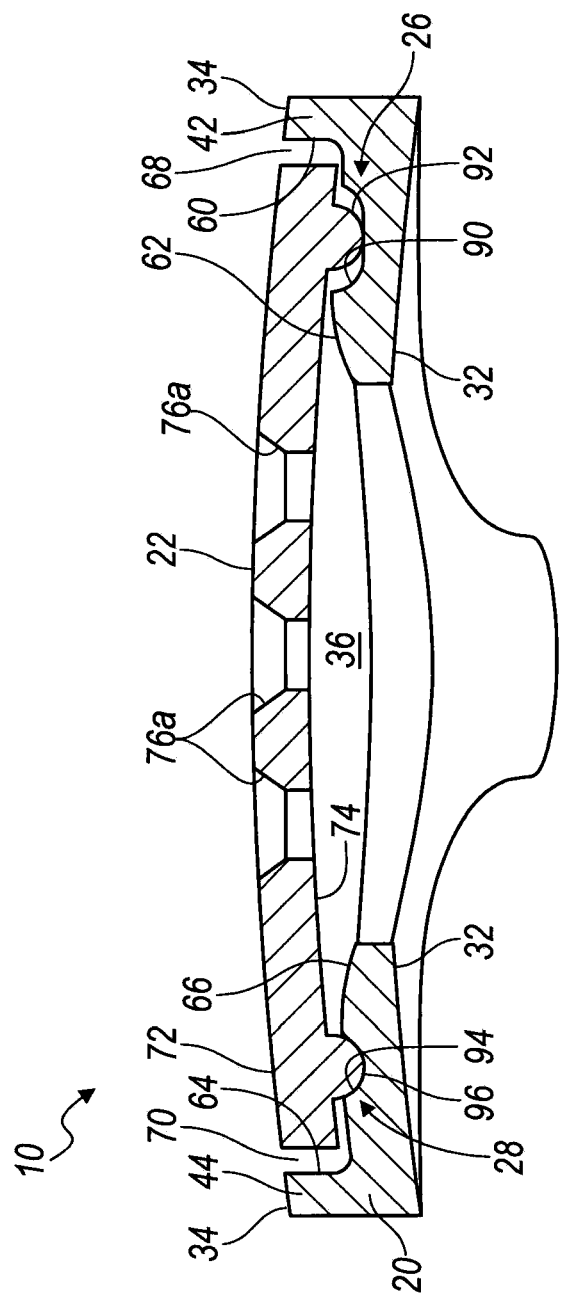
FIG. 5 is a cross-sectional side view of the plate assembly of FIG. 1 taken along line 5-5.
Figure 6:
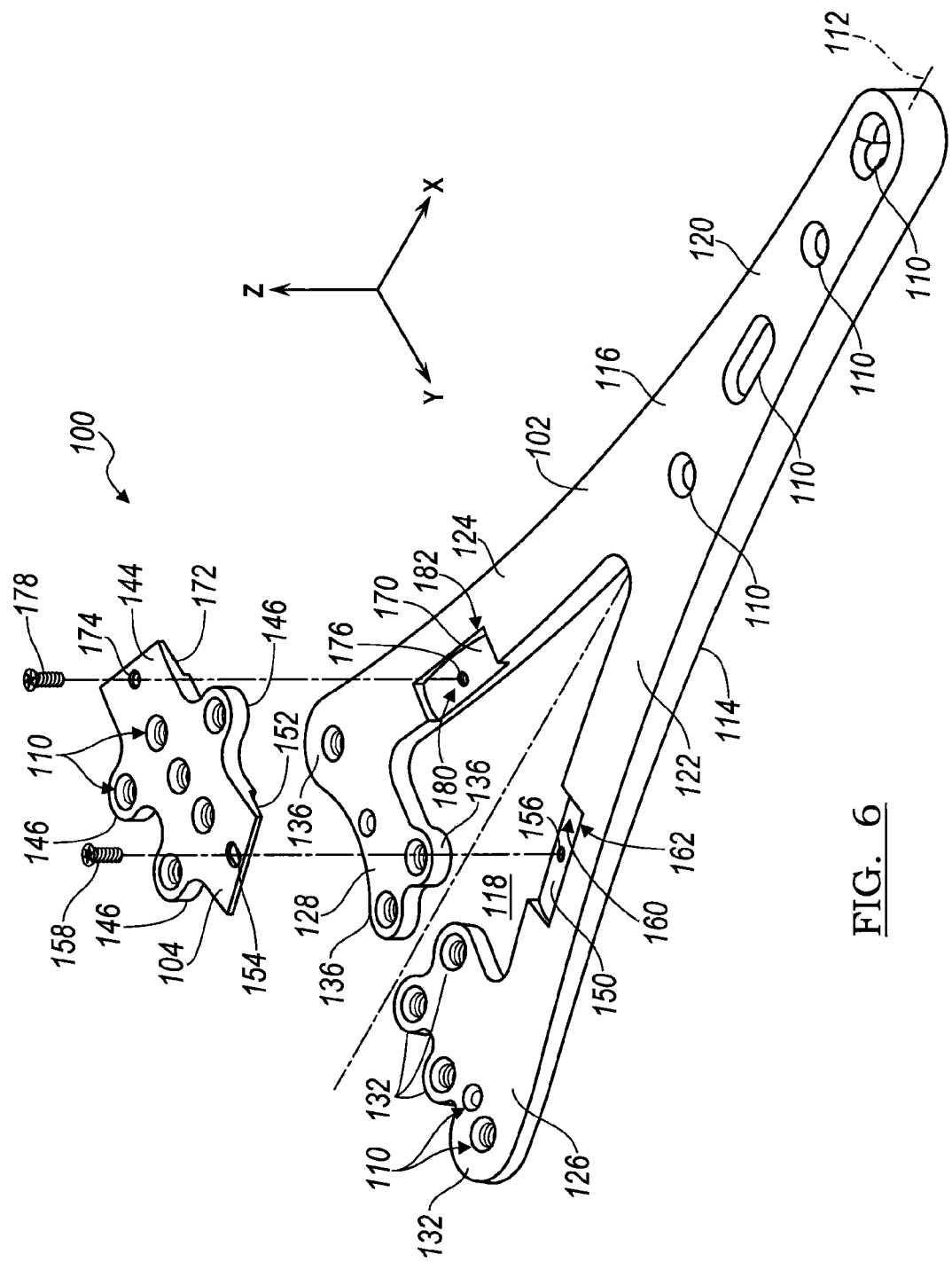
FIG. 6 is an exploded perspective view of another orthopedic plate assembly according to the present disclosure.

The support member 22 can generally be smooth and thin and can have a width (y-direction) that enables the support member 22 to span the aperture 36, and at opposite ends, to engage the plate member 20. The support member 22 can be formed to have a pre-contoured shape based on the morphology of the bone to which the support member 22 is to be secured and the pre-contoured shape of the plate member 20. The support member 22 can generally have a curved or arcuate shape as shown (FIG. 5). When engaged, the outer surface 72 can be flush or nearly flush with an adjoining portion of the outer surface 34 of the plate member.

The support member 22 can include a sixth contouring region 80 having a predetermined sixth stiffness. A length (x-direction) and a thickness (z-direction) of the support member 22 along the width can vary. The length and the thickness can be selected to provide the support member 22 with the sixth stiffness. In the present example, the length and the thickness can be generally constant along the width.

The support member 22 can include a predetermined number and arrangement of the holes 24. According to the present example, the support member 22 can include three bone screw holes 76 spaced apart along a center line of the support member 22. The support member 22 can further include portions of the first and second engagement members 26, 28.

The first engagement member 26 can be disposed at a first interface between the plate member 20 and the end of the support member 22 received by the first recess 60. The first engagement member 26 can include a first bearing or engaging component 90 and a second bearing or engaging component 92. The first bearing component 90 can be coupled to the plate member 20 and the second bearing component 92 can be coupled to the support member 22. The first and second bearing components 90, 92 can be coupled in any suitable manner. The first bearing component 90 can be formed integral with the plate member 20, as illustrated by the present example. Similarly, the second bearing component 92 can be formed integral with the support member 22.

The first bearing component 90 can directly engage the second bearing component 92 when the support member 22 is engaged with the plate member 20. When engaged, the first bearing component 90 can receive the second bearing component 92. The first and second bearing components 90, 92 can cooperate and thereby constrain relative translational movement between the first and second bearing components 90, 92 in at least one direction. According to the present example, the first bearing component 90 can constrain relative movement in a first direction (x-direction) perpendicular to a second direction (z-direction) in which the first and second bearing components 90, 92 engage. The first bearing component 90 can permit relative translational movement in a third direction (y-direction) perpendicular to both the first and second directions.

In various implementations, the first bearing component 90 can be a first concavity defining a recess and the second bearing component 92 can be a first convexity. In the present example, the first bearing component 90 can be a slot formed by the bottom surface 62 having a curved bottom forming curved sidewalls of the slot. A length of the slot (y-direction) can be selected to permit a predetermined amount of relative translational movement. The second bearing component 92 can be a hemispherical convexity formed by the inner surface 74 to complement the sidewalls.

The second engagement member 28 can be disposed at a second interface between the plate member 20 and the end of the support member 22 received by the second recess 64. The second engagement member 28 can include a third bearing or engaging component 94 and a fourth bearing or engaging component 96. The third bearing component 94 can be coupled to the plate member 20 and the fourth bearing component 96 can be coupled to the support member 22. The first and second bearing components 90, 92 can be coupled in any suitable manner and can be formed integral with the plate member 20 and the support member 22, as illustrated by the present example.

The third bearing component 94 can directly engage the fourth bearing component 96 when the support member 22 is engaged with the plate member 20. When engaged, the third bearing component 94 can receive the fourth bearing component 96. The third and fourth bearing components 94, 96 can cooperate and thereby constrain relative translational movement between the third and fourth bearing components 94, 96 in at least two directions. According to the present example, the first and second bearing components 94, 96 can constrain relative translational movement in a first direction (x-direction) perpendicular to a second direction (z-direction) in which the third and fourth bearing components 94, 96 engage. The third and fourth bearing components 94, 96 can further constrain relative translational movement in a third direction (y-direction) perpendicular to the first and second directions.

In various implementations, the third bearing component 94 can be a second concavity defining a recess and the fourth bearing component 96 can be a second convexity. In the present example, the third bearing component 94 can be a hemispherical concavity formed by the bottom surface 66. The fourth bearing component 96 can be a hemispherical convexity formed by the inner surface 74 to complement the third bearing component 94. The third and fourth bearing components 94, 96 can form a ball-and-socket-type joint.

With continued reference to FIGS. 1-5, a method for supporting a fractured bone (e.g., bone 16) using the plate assembly 10 will now be described. Generally, the method includes exposing the bone 16, selecting and selectively re-contouring the plate member 20 and the support member 22, engaging the plate member 20 and the support member 22, and securing the plate member 20 and the support member 22 to the fragments 12, 14 of the bone 16. It will be appreciated that the bone 16 can be exposed prior to or after selecting and/or re-contouring the plate member 20 and the support member 22. It will be further appreciated that the order of engaging the plate member 20 and the support member 22 and securing the plate member 20 and the support member 22 to the bone can vary.

The bone 16 can be exposed using a suitable surgical procedure. The plate member 20 and the support member 22 can be individually selected for a particular patient from a group of pre-fabricated support members 22 and plate members 20 provided in various sizes and pre-contoured shapes. As discussed above, the plate member 20 and the support member 22 can have pre-contoured shapes designed to match the exterior shape of the bone 16. Additionally, the holes 24 formed in the plate member 20 and the support member 22 can be configured to receive the various attachment devices at predetermined trajectories. Due to variation in bone shape, the pre-contoured shapes of the selected components may not match the patient's bone as closely as desired. Due to variation in fracture patterns, the predetermined trajectories of one or more of the holes 24 may not provide a desired trajectory for attachment with a particular fragment of the fractured bone.

As desired, the selected plate member 20 and the support member 22 can be independently re-contoured to more closely match the patient's bone and adjust the trajectories allowed by the holes 24. More specifically, the body 40, the first and second arms 42, 44, the first and second tabs 46, 48, and the support member 22 can be independently re-contoured as desired. Re-contouring can be performed in the various re-contouring regions 50, 52a, 52b, 54a, 54b, 80. Among the re-contouring regions 50, 52a, 52b, 54a, 54b, 80, the stiffness can vary to facilitate independent re-contouring. As one example, the fourth stiffness of the first tab 46 and the fifth stiffness of the second tab 48 can be less than the second stiffness of the first arm 42 and the third stiffness of the second arm 44. Additionally, the second and third stiffness of the first and second arms 42, 44 can be less than the first stiffness of the body 40.

Re-contouring can be performed by bending and/or twisting the plate member 20 and the support member 22 using one or more bending tools. For example, the first and second arms 42, 44 can be independently bent about the y-axis and/or twisted about the x-axis. The first and second tabs 46, 48 can be bent about the x-axis and y-axis and can be twisted about the y-axis. It will be appreciated that independent re-contouring relative to one or more of the x-axis, the y-axis, and the z-axis can be performed as desired. The bending tools can engage various surfaces and features of the plate member 20 and the support member 22. For example, the bending tools can engage the bone engaging surface 32 and the outer surface 34 of the plate member 20, and/or can engage the outer and inner surfaces 72, 74 of the support member 22. The bending tools can also engage one or more of the holes 24 during re-contouring.

Once re-contoured to the desired shape, the plate member 20 can be secured to one or both the fragments 12, 14 of the bone 16 using the bone screws 18. While two bone fragments 12, 14 are shown for exemplary purposes, additional bone fragments may be present. The plate member 20 can be secured to one or more of the additional bone fragments as desired. Subsequently, the re-contoured support member 22 can be disposed on and brought into engagement with the plate member 20 via the first and second engagement members 26, 28. Once engaged, the support member 22 can be secured to one or both the fragments 12, 14 of the bone 16 using the bone screws 18. Alternately, the support member 22 can be brought into engagement while securing the support member 22 to one or both the fragments 12, 14 using the bone screws 18.

In an exemplary sequence according to the present example, the body 40 and the second tab 48 can be attached to the fragment 14 in that order. When attaching the body 40, the slotted hole 76*d* can be used first to secure the plate member 20 in a desired longitudinal position along the bone 16. Subsequently, one or more of the holes 76*a*, 76*b*, 76*d* can be used to attach the plate member 20 to the fragment 14. Next, the support member 22 can be attached to the fragment 14. Subsequently, the first tab 46 can be attached to the fragment 12.

With reference to FIGS. 6-9, another exemplary orthopedic plate assembly 100 for internal fixation of two or more fragments of a fractured bone is presented. For clarity, various features of the plate assembly 100 will be described with reference to coordinate axes shown in FIG. 6. The plate assembly 100 can be configured to attach to the distal, volar aspect of a fractured radius in a similar manner as the plate assembly 10. Generally, the plate assembly 100 can include a bifurcated plate member 102, a support member 104, a first engagement member 106, a second engagement member 108, and a plurality of holes 110 for receiving suitable attachment devices (e.g., bone screws 18).

The plate member 102 can have a length along a center line 112 and can include a bone engaging surface 114, an outer surface 116, an aperture 118, and a predetermined number of the holes 110. In FIGS. 6-9, the center line 112 is shown to extend along the x-axis. The bone engaging surface 114 and the outer surface 116 can be substantially similar to the bone engaging surface 32 and the outer surface 34 of the plate assembly 10. When formed, the plate member 102 can have a pre-contoured shape based on the typical morphology of the bone (e.g., bone 16) to which the plate member 102 is to be secured. The holes 110 can be substantially similar to the holes 24 and can have a predetermined arrangement selected in a manner similar the holes 24.

The plate member 102 can further include a body 120, a first arm 122, a second arm 124, a first tab 126, and a second tab 128. The body 120, the first and second arms 122, 124, and the first and second tabs 126, 128 can be substantially similar to the body 40, first and second arms 42, 44, and first and second tabs 46, 48. For brevity, the differences between the plate member 102 and the plate member 20 will be described in further detail.

The first tab 126 can be attached to the same or a different bone fragment than the body 120. The first tab 126 can include a first tab body 130, one or more first extensions 132, and a predetermined number and arrangement of the holes 110. The first tab body 130 can extend from an end of the first arm 122 opposite the body 120, and can extend transverse to the first arm 122. The first tab body 130 can include a portion of the bone engaging surface 114 and a portion of the outer surface 116.

The first extensions 132 can extend from the first tab body 130 in various transverse directions. For example, the first extensions 132 can extend parallel to the center line 112, parallel to the direction in which the first tab body 130 extends, and/or in oblique directions with respect to the center line 112 and the first tab body 130. The number, arrangement, and orientation of the first extensions 132 can be predetermined based on bone morphology and typical fracture patterns. According to the present example, the first tab 126 can include four first extensions arranged as shown.

One or more of the first extensions 132 can be configured to attach to the bone. According to the present example, each of the first extensions 132 can include one of the holes 110 for attachment to the bone. The first extensions 132 can form additional contouring regions that enable independent re-contouring of the first extensions 132 to more closely match the bone and/or vary the trajectories of respective bone screws. The first extensions 132 can be sized to provide each of the associated contouring regions with a predetermined stiffness. Among the first extensions 132, the stiffness can vary. In FIG. 7, exemplary boundaries of the additional contouring regions are illustrated by the dashed lines.

The second tab 128 can be attached to the same or a different bone fragment than the body 120 and/or the first tab 126. The second tab 128 can include a second tab body 140, one or more second extensions 142, and a predetermined number of the holes 110. The second tab body 140 can extend from an end of the second arm 124 opposite the body 120, and can extend transverse to the second arm 124. The second tab body 140 can include a portion of the bone engaging surface 114 and a portion of the outer surface 116.

The second extensions 142 can extend from the second tab body 140 in various transverse directions. The number, arrangement, and orientation of the second extensions 142 can be predetermined based on bone morphology and typical fracture patterns. According to the present example, the second tab 128 can include three first extensions arranged as shown. One or more of the second extensions 142 can be configured to attach to the bone. According to the present example, each of the second extensions 142 can include one of the holes 110 for attachment to the bone. The second extensions 142 can form additional contouring regions that enable independent re-contouring of the second extensions 142 to more closely match the bone and/or vary the trajectories of respective bone screws. The second extensions 142 can be sized to provide each of the associated contouring regions with a predetermined stiffness. Among the second extensions 142, the stiffness can vary. In FIG. 7, the additional contouring regions are illustrated by dashed lines.

Figure 9:
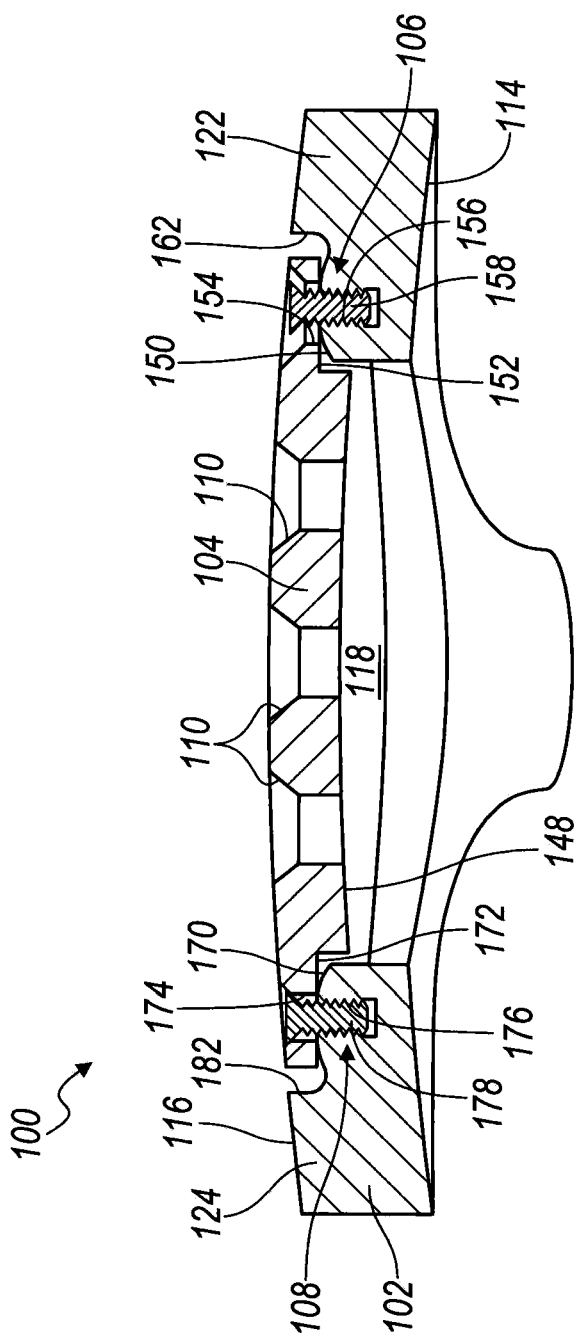
FIG. 9 is a cross-sectional side view of the plate assembly of FIG. 6 taken along line 9-9.

The support member 104 can have a pre-contoured shape based on the bone morphology and the pre-contoured shape of the plate member 102. The support member 104 can include a support body 144, third extensions 146, and a predetermined number and arrangement of the holes 110. The support body 144 can have a width (y-direction) that enables the support body 144 to span the aperture 118 and can include an inner surface 148 that engages the plate member 102 at opposite ends of the support member 104. The inner surface 148 can include shoulders and can extend within the aperture 118 between the bone engaging surface 114 and the outer surface 116 as shown (FIG. 9).

The third extensions 146 can extend from the support body 144 in various transverse directions. The number, arrangement, and orientation of the third extensions 146 can be predetermined based on bone morphology and typical fracture patterns. One or more of the third extensions 146 can be configured to attach to the bone. According to the present example, each of the third extensions 146 can include one of the holes 110 for attachment to the bone. The third extensions 146 can form additional contouring regions and can be sized to provide each of the associated contouring regions with a predetermined stiffness. Among the third extensions 146, the stiffness can vary. In FIG. 7, the additional contouring regions are illustrated by dashed lines.

The first engagement member 106 can be disposed at a first interface between the plate member 102 at a first end of the support member 104. The first interface can be disposed at the first arm 122. The first engagement member 106 can include a first bearing or engaging component 150, a second bearing or engaging component 152, an elongated hole 154, a first threaded hole 156, and a first threaded fastener 158.

The first bearing component 150 can be disposed on a transverse surface 160 of a first recess 162 formed in the outer surface 116 that receives the first end of the support member 104. The first recess 162 and the first bearing component 150 can be formed integral with the first arm 122. The first bearing component 150 can include a convex, curved first bearing surface that directly engages the second bearing component 152. Through re-contouring, the first bearing component 150 can engage the second bearing component 152 at various contact angles. Accordingly, the first bearing surface can be curved to provide a suitable contact surface between the first and second bearing components 150, 152 over a predetermined range of contact angles.

The second bearing component 152 can be disposed at the first end of the support body 144 on the inner surface 148. The second bearing component 152 can be formed integral with the support body 144. The second bearing component 152 can include a generally flat, second bearing surface that directly engages the first bearing component 150. Alternately, the second bearing surface can be a concave, curved surface complementary with the first bearing surface.

The elongated hole 154 can be formed in and extend along the width of the support body 144 at the first end. The elongated hole 154 can be configured to receive the first threaded fastener 158 at various angles corresponding to the predetermined range of contact angles between the first and second bearing components 150, 152. For example, the elongated hole 154 can be chamfered and can be sized larger than a threaded portion of the first threaded fastener 158. The chamfer of the elongated hole 154 can be sized to constrain translational movement of the first threaded fastener 158 in a first direction (x-direction). The elongated hole 154 can have a predetermined width (y-direction) for receiving the first threaded fastener 158 at various positions along the width.

The first threaded hole 156 can be formed in and extend through the first bearing component 150. The first threaded hole 156 can be configured to threadingly engage the first threaded fastener 158. The first threaded fastener 158 can be configured to engage the elongated hole 154 and threadingly engage the first threaded hole 156.

The second engagement member 108 can be disposed at a second interface between the plate member 102 at a second end of the support member 104 opposite the first end. The second interface can be disposed at the second arm 124. The second engagement member 108 can include a third bearing or engaging component 170, a fourth bearing or engaging component 172, a circular hole 174, a second threaded hole 176, and a second threaded fastener 178.

The third bearing component 170 can be disposed on a transverse surface 180 of a second recess 182 formed in the outer surface 116 that receives the second end of the support member 104. The second recess 182 and the third bearing component 170 can be formed integral with the second arm 124. The third bearing component 170 can include a convex, curved third bearing surface that directly engages the fourth bearing component 172. Through re-contouring, the third bearing component 170 can engage the fourth bearing component 172 at various contact angles. Accordingly, the third bearing surface can be curved to provide a suitable contact surface between the third and fourth bearing components 170, 172 over a predetermined range of contact angles.

The fourth bearing component 172 can be disposed at the second end of the support body 144 on the inner surface 148. The fourth bearing component 172 can be formed integral with the support body 144. The fourth bearing component 172 can include a generally flat, fourth bearing surface that directly engages the third bearing component 170. Alternately, the fourth bearing surface can be a concave, curved surface complementary with the third bearing surface.

The circular hole 174 can be formed in the support body 144 at the second end. The circular hole 174 can be configured to receive the second threaded fastener 178 at various angles. For example, the circular hole 174 can be chamfered and can be sized larger than a threaded portion of the second threaded fastener 178. The chamfer of the circular hole 174 can be sized to constrain translational movement of the second threaded fastener 178 in both a first direction (x-direction) and a second direction (y-direction) perpendicular to the first direction.

The second threaded hole 176 can be formed in and extend through the third bearing component 170. The second threaded hole 176 can be configured to threadingly engage the second threaded fastener 178. The second threaded fastener 178 can be configured to engage the circular hole 174 and threadingly engage the second threaded hole 176.

With continued reference to FIGS. 6-9, the plate assembly 100 can be used in a method for supporting a fractured bone that is substantially similar to the procedure described above with reference to the plate assembly 10. The plate assembly 100 can be attached to the bone in a substantially similar manner as the plate assembly 10. However, it will be appreciated that the support member 104 can be attached to the plate member 102 without attaching the support member 104 to the bone via the threaded fasteners 158, 178 of the first and second engagement members 106, 108. When attached in this manner, the plate member 102 can be attached to various bone fragments and the support member 104 can provide additional support for retaining the plate member 102 in a desired shape.

The plate assembly 100 can provide additional independent re-contouring capability. The additional re-contouring capability can be provided via the various first and second extensions 132, 142 provided with the plate member 102 and the various third extensions 146 provided with the support member 104. Each of the first, second, third extensions 132, 142, 146 can be independently re-contoured to more closely match the unique shape of the patient's bone. Alternately or additionally, each of the first, second, third extensions 132, 142, 146 can be independently re-contoured to provide a desired trajectory for a bone screw 18 or other suitable attachment device.

Figure 10:
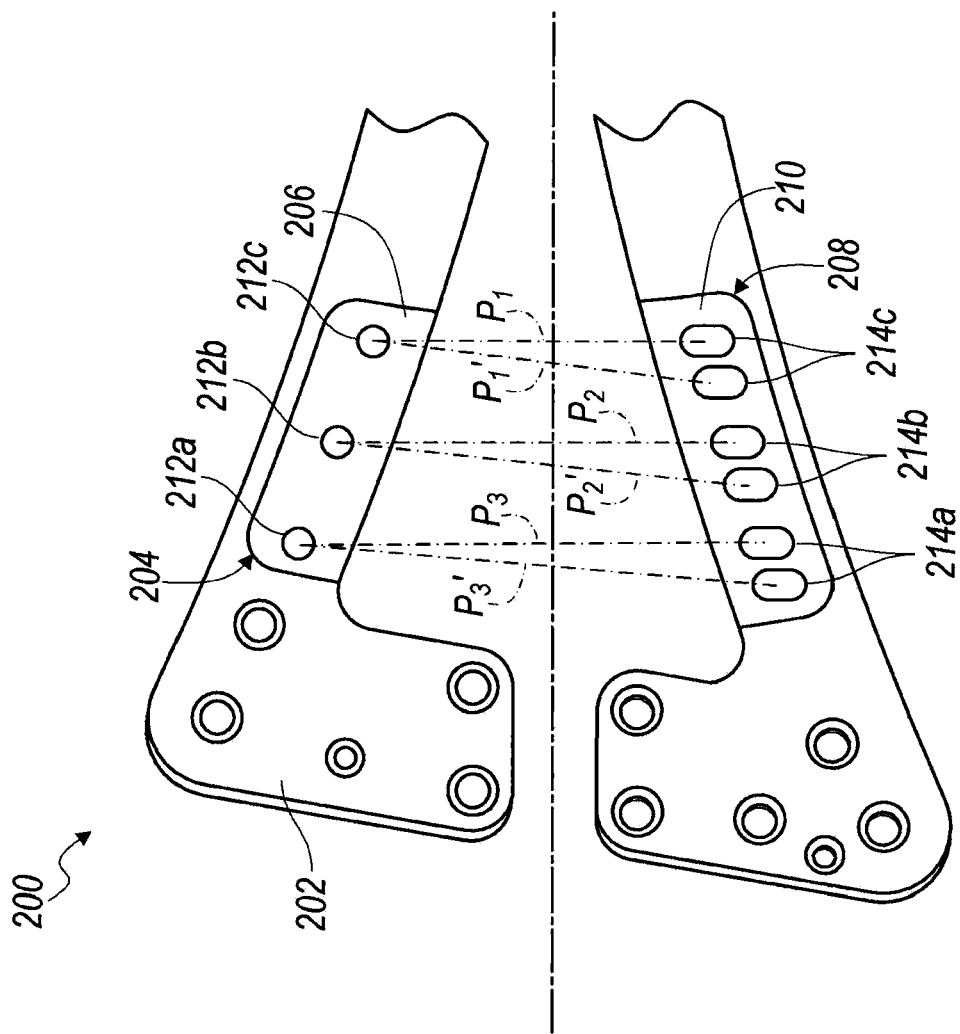
FIG. 10 is a top view of a portion of another orthopedic plate assembly according to the present disclosure.

With reference to FIG. 10, another exemplary orthopedic plate assembly 200 for internal fixation of two or more fragments of a fractured bone is presented. The plate assembly 200 is substantially similar to the plate assembly 10, except that plate assembly 200 can receive a support member (e.g., support member 22) at various predetermined longitudinal positions. Accordingly, for brevity, the differences between the plate assembly 200 and the plate assembly 10 will be described in further detail. The plate assembly 200 can include a plate member 202 including a first elongated slot 204 having a transversely extending first bottom surface 206, and a second elongated slot 208 having a transversely extending second bottom surface 210. The first and second elongated slots 204, 208 can be configured to receive opposite ends of the support member at various predetermined longitudinal positions along a length of the plate member 202.

The plate member 202 can further include concavities 212a, 212b, 212c and pairs of slots 214a, 214b, 214c for engagement with the support member. The concavities 212a, 212b, 212c can be substantially similar to the third bearing component 94 of the plate member 20. The slots 214a, 214b, and 214c can be substantially similar to the first bearing component 90 of the plate member 20.

The concavities 212a, 212b, 212c and the pairs of slots 214a, 214b, 214c can be arranged to allow the support member to engage the plate member 202 using various combinations of the concavities 212a, 212b, 212c and the pairs of slots 214a, 214b, 214c. In an exemplary arrangement, the support member can engage the plate member 202 at various longitudinal positions and orientations as illustrated by dashed lines $P_1$, $P_2$, $P_3$ and dashed lines $P_1'$, $P_2'$, $P_3'$. Accordingly, it will be appreciated that the plate member 202 can be configured to receive the support member at various longitudinal positions and at various transverse angles.

The foregoing description of the examples has been provided for purposes of illustration and description. It is not intended to be exhaustive or to limit the present teachings. Individual elements or features of a particular example are generally not limited to that particular example, but, where applicable, are interchangeable and can be used in a selected example, even if not specifically shown or described. The same may also be varied in many ways. Such variations are not to be regarded as a departure from the present teachings, and all such modifications are intended to be included within the scope of the present teachings.

What is claimed is:

1. An orthopedic plate assembly for supporting a bone, comprising:
a y-shaped first plate attachable to the bone and having a center line, the first plate including an elongate body attachable to a first portion of the bone and extending along the center line from a first end to a second end of the body, a first arm transversely extending away from the center line at a first angle from the second end of the body, and a second arm transversely extending away from the center line at a second angle from the second end of the body to form the y-shaped first plate, the first and second arms defining a triangularly shaped aperture between the first and second arms in the first plate; and
a second plate separate from the first plate and attachable to the bone, the second plate having a first end configured to be disposed on and engaged with the first arm, and a second end opposite the first end configured to be disposed on and engaged with the second arm, the second plate configured to span the triangularly shaped aperture transverse to the center line when engaged with the first and second arms;
wherein the second plate is configured to engage the first arm in a first recess formed in a central region of the first arm between the body and an end of the first arm opposite the body, and to engage the second arm in a second recess formed in a central region of the second arm between the body and an end of the second arm opposite the body, wherein upon engaging the second plate to the first plate, an outer surface of the second plate is flush with an outer surface of the first plate.

2. The orthopedic plate assembly of claim 1, wherein the first plate further includes a first tab extending from the end of the first arm opposite the body in a first direction transverse to and toward the center line; and a second tab extending from the end of the second arm opposite the body in a second direction transverse to and toward the center line, and wherein the first and second tabs are separated by a gap extending along the center line, and at least one of the first tab and the second tab is attachable to the bone, wherein the first and second tabs each define a plurality of bone screw holes through each of the first and second tabs.

3. The orthopedic plate assembly of claim 2, wherein the second plate is configured to engage the first arm between the body and the first tab, and to engage the second arm between the body and the second tab, wherein the second plate is arcuate from the first end to the second end of the second plate.

4. The orthopedic plate assembly of claim 2, wherein the first tab includes an extension that extends from the first tab in a third direction transverse to the first direction in which the first tab extends.

5. The orthopedic plate assembly of claim 2, wherein a predetermined first stiffness of the first tab is less than a predetermined second stiffness of the first arm, and wherein the predetermined second stiffness is less than a predetermined third stiffness of the body, wherein a thickness of the first plate tapers from a first thickness at the first end of the body to a second thickness at the first and second tabs, where the thickness progressively thins to provide progressively more malleability toward the first and second tabs.

6. The orthopedic plate assembly of claim 1, wherein the second plate includes an extension that extends from the second plate in a first direction transverse to a second direction between the first and second ends of the second plate.

7. The orthopedic plate assembly of claim 1, wherein a threaded connection is formed between the first and second plates.

8. An orthopedic plate assembly for supporting a bone, comprising:
a y-shaped first plate attachable to the bone and having a center line, the first plate including an elongate body attachable to a first portion of the bone and extending along the center line from a first end to a second end of the body, a first arm transversely extending away from the center line at a first angle from the second end of the body, and a second arm transversely extending away from the center line at a second angle from the second end of the body to form the y-shaped first plate, the first and second arms defining a triangularly shaped aperture between the first and second arms in the first plate; and
a second plate separate from the first plate and attachable to the bone, the second plate having a first end configured to be disposed on and engaged with the first arm, and a second end opposite the first end configured to be disposed on and engaged with the second arm, the second plate configured to span the triangularly shaped aperture transverse to the center line when engaged with the first and second arms;

wherein the first plate includes a first major surface engageable with the bone and a second major surface opposite the first major surface, and wherein the second plate is received within a first recess formed in the second major surface and disposed on the first arm, and a second recess formed in the second major surface and disposed on the second arm, wherein an outer surface of the second plate is substantially co-planar to the second major surface when received in the first and second recesses.

9. An orthopedic plate assembly for supporting a bone, comprising:
a y-shaped first plate attachable to the bone and having a center line, the first plate including an elongate body attachable to a first portion of the bone and extending along the center line from a first end to a second end of the body, a first arm transversely extending away from the center line at a first angle from the second end of the body, and a second arm transversely extending away from the center line at a second angle from the second end of the body to form the y-shaped first plate, the first and second arms defining a triangularly shaped aperture between the first and second arms in the first plate; and
a second plate separate from the first plate and attachable to the bone, the second plate having a first end configured to be disposed on and engaged with the first arm, and a second end opposite the first end configured to be disposed on and engaged with the second arm, the second plate configured to span the triangularly shaped aperture transverse to the center line when engaged with the first and second arms;
a first bearing component coupled to the first arm; and a second bearing component coupled to the first end of the second plate, wherein the first and second bearing components cooperate and thereby constrain relative translational movement between the first plate and the second plate in at least two perpendicular directions when the second plate is engaged with the first plate;
wherein the first and second bearing components are configured to form a ball-and-socket type joint.

10. The orthopedic plate assembly of claim 9, further comprising a third bearing component coupled to the second arm; and a fourth bearing component coupled to the second end of the second plate, wherein the third and fourth bearing components cooperate and thereby constrain relative translational movement between the first plate and the second plate in a single direction only when the second plate is engaged with the first plate, wherein the third and fourth bearing components are configured to form a ball-and-slot type joint, where the slot is transverse to the center line.

11. The orthopedic plate assembly of claim 9, further comprising a third bearing component coupled to the first arm and longitudinally spaced apart from the first bearing component, wherein the third bearing component is configured to cooperate with the second bearing component and thereby constrain relative translational movement between the first plate and the second plate in at least two perpendicular directions.

12. An orthopedic plate assembly for supporting a fractured radius, comprising:
a first plate attachable to a first bone fragment and a second bone fragment of the radius and having a center line, the first plate including an elongate body attachable to the first fragment and extending along the center line, a first arm transversely extending away from the center line at a first angle from an end of the body, and a second arm transversely extending away from the center line at a second angle from the end of the body, the first and second arms defining a triangularly shaped aperture in the first plate;
a second plate separate from the first plate, the second plate including a first transverse surface on a first end engageable with a second transverse surface of the first arm, and a third transverse surface on a second end opposite the first end engageable with a fourth transverse surface of the second arm; and
a first engagement member configured to constrain relative translational movement between the first and second plates in at least two perpendicular directions when engaged, the first engagement member including a first bearing component coupled to the first transverse surface of the second plate, and a second bearing component coupled to the second transverse surface of the first arm and directly engageable with the first bearing component,
wherein the second plate is configured to span the aperture transverse to the center line when engaged with the first and second arms;
wherein the first and second bearing components form a ball-and-socket type joint when engaged.

13. The orthopedic plate assembly of claim 12, wherein the second plate is attachable to at least one of the first and second bone fragments.

14. The orthopedic plate assembly of claim 12, wherein the first plate further includes a first tab extending from an end of the first arm opposite the body in a first direction transverse to and toward the center line; and a second tab extending from an end of the second arm opposite the body in a second direction transverse to and toward the center line, and wherein the first and second tabs are separated by a gap and at least one of the first tab and the second tab is attachable to at least one of the first and second bone fragments, wherein the first and second tabs each define a plurality of bone screw holes through each of the first and second tabs.

15. The orthopedic plate assembly of claim 14, wherein a predetermined first stiffness of the first tab is less than a predetermined second stiffness of the first arm, and wherein the predetermined second stiffness is less than a predetermined third stiffness of the body, wherein a thickness of the first plate tapers from a first thickness at a first end of the body to a second thickness at the first and second tabs, where the thickness progressively thins to provide progressively more malleability toward the first and second tabs.

16. The orthopedic plate assembly of claim 12, further comprising a second engagement member configured to constrain relative translational movement between the first and second plates in at least one direction when engaged, the second engagement member including a third bearing component coupled to the third transverse surface of the second plate, and a fourth bearing component coupled to the fourth transverse surface of the second arm and mateably engageable with the third bearing component, wherein the third and fourth bearing components are configured to form a ball-and-slot type joint, where the slot is transverse to the center line.

17. An orthopedic plate assembly for supporting a bone, comprising:
an elongated body extending along a center line from a first end to a second end;
a first arm extending from the second end of the body away from and at a first angle to the center line;
a second arm extending from the second end of the body away from and at a second angle to the center line;
a first tab extending from an end of the first arm opposite the body in a first direction transverse to and toward the center line, the first tab defining a plurality of bone screw holes extending through the first tab;

a second tab extending from an end of the second arm opposite the body in a second direction transverse to and toward the center line, the second tab defining a plurality of bone screw holes through the second tab, wherein the first and second tabs define a gap extending substantially along the center line and the first and second arms and the first and second tabs define a triangularly shaped aperture between the first and second arms; and a separate support plate having a first end configured to be disposed on and engaged with the first arm, and a second end opposite the first end configured to be disposed on and engaged with the second arm, the support plate configured to span the triangularly shaped aperture transverse to the center line when engaged with the first and second arms; wherein the first arm defines a first recess and the second arm defines a second recess, the first recess configured to receive the first end of the support plate and the second recess configured to receive the second end of the support plate, wherein an outer surface of the support plate is substantially flush with an outer surface of the first arm and an outer surface of the second arm.

18. The orthopedic plate assembly of claim 17, further comprising a first bearing component at the first end of the support plate and a second mating bearing component in the first recess of the first arm; and a third bearing component at the second end of the support plate and a fourth mating bearing component in the second recess of the second arm, wherein the first and second bearing components and the third and fourth bearing components are configured to be engaged respectively upon engaging the support plate to the first and second arms.

19. The orthopedic plate assembly of claim 18, wherein the first and second bearing components are configured to form a ball-and-socket type joint and wherein the third and fourth bearing components are configured to form a ball-and-slot type joint, where the slot extends transverse to the center line.

20. The orthopedic plate assembly of claim 17, wherein the support plate is configured to be retained relative to the first and second arms with a bone screw passing only through a hole in the support plate.

* * * * *

UNITED STATES PATENT AND TRADEMARK OFFICE
CERTIFICATE OF CORRECTION

PATENT NO. : 8,518,042 B2  
APPLICATION NO. : 12/907626  
DATED : August 27, 2013  
INVENTOR(S) : Nathan A. Winslow et al.

Page 1 of 1

It is certified that error appears in the above-identified patent and that said Letters Patent is hereby corrected as shown below:

In the Specification

Column 9, Line 65, Delete "94, 96" and insert --90, 92--.

Signed and Sealed this  
Twenty-ninth Day of April, 2014

Michelle K. Lee  
*Deputy Director of the United States Patent and Trademark Office*